(12) United States Patent
Akahori et al.

(10) Patent No.: US 8,808,621 B2
(45) Date of Patent: Aug. 19, 2014

(54) LIQUID-MIXING APPARATUS, CHEMICAL TESTING APPARATUS, AND ENDOSCOPE PROCESSING APPARATUS

(75) Inventors: Hiromasa Akahori, Hachioji (JP); Shinichiro Kawachi, Chofu (JP); Jiro Komiya, Hachioji (JP); Hisashi Kuroshima, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 123 days.

(21) Appl. No.: 13/098,734

(22) Filed: May 2, 2011

(65) Prior Publication Data

US 2011/0268611 A1 Nov. 3, 2011

Related U.S. Application Data

(63) Continuation of application No. PCT/JP2010/070606, filed on Nov. 18, 2010.

(30) Foreign Application Priority Data

Jan. 8, 2010 (JP) ................................. 2010-003197

(51) Int. Cl.
*A61L 2/16* (2006.01)
*A61B 1/12* (2006.01)

(52) U.S. Cl.
CPC ................. *A61B 1/123* (2013.01); *A61B 1/125* (2013.01); *A61B 1/126* (2013.01)
USPC ................. 422/28; 422/1; 422/292; 422/297; 422/300

(58) Field of Classification Search
CPC .......... A61B 1/12; A61B 1/123; A61B 1/125; A61B 1/126
USPC ................................. 422/1, 28, 292, 297, 300
See application file for complete search history.

(56) References Cited

U.S. PATENT DOCUMENTS

| 5,951,161 A | 9/1999 | Blagg | |
|---|---|---|---|
| 2002/0175183 A1 | 11/2002 | Schell et al. | |
| 2003/0037829 A1 | 2/2003 | Wilson | |
| 2005/0150831 A1* | 7/2005 | Tabani et al. | 210/636 |
| 2008/0152539 A1* | 6/2008 | Kawachi et al. | 422/28 |

FOREIGN PATENT DOCUMENTS

| JP | 02-041133 | 2/1990 |
|---|---|---|
| JP | 07-081981 | 3/1995 |
| JP | 08-004067 | 1/1996 |

(Continued)

OTHER PUBLICATIONS

Supplementary European Search Report mailed Dec. 16, 2011 in corresponding International Patent Application No. EP10842148.

*Primary Examiner* — Lyle Alexander
(74) *Attorney, Agent, or Firm* — Scully, Scott, Murphy & Presser, P.C.

(57) ABSTRACT

A liquid mixing apparatus of the present invention includes: a first tank; a first introduction section that introduces a first liquid into the first tank; a second introduction section that introduces a second liquid into the first tank; a first opening portion provided above a highest liquid level of the first tank; a second tank; a third introduction section that introduces a third liquid into the second tank; a second opening portion provided above a highest liquid level of the second tank; a liquid transfer conduit that connects a bottom surface portion of the first tank and a bottom surface portion of the second tank; an opening/closing valve provided in the liquid transfer conduit; a gas transfer conduit having one end arranged above the highest liquid level in the first tank and another end arranged above the highest liquid level in the second tank; a pump capable of forward/reverse operation that can transfer a gas in two directions inside the gas transfer conduit; and an atmospheric release control section that controls opening and closing of the first opening portion and the second opening portion.

4 Claims, 9 Drawing Sheets

(56) References Cited

FOREIGN PATENT DOCUMENTS

| | | |
|---|---|---|
| JP | 08-136451 | 5/1996 |
| JP | 2004-016638 | 1/2004 |
| JP | 2008-142420 | 6/2008 |
| JP | 2009-172012 | 8/2009 |

\* cited by examiner

LIQUID-MIXING APPARATUS, CHEMICAL TESTING APPARATUS, AND ENDOSCOPE PROCESSING APPARATUS

CROSS REFERENCE TO RELATED APPLICATION

This application is a continuation application of PCT/JP2010/070606 filed on Nov. 18, 2010 and claims benefit of Japanese Application No. 2010-003197 filed in Japan on Jan. 8, 2010, the entire contents of which are incorporated herein by this reference.

BACKGROUND OF THE INVENTION

1. Field of the Invention

The present invention relates to a liquid mixing apparatus that mixes a plurality of liquids at a predetermined ratio, and to a chemical testing apparatus and an endoscope processing apparatus that include the liquid mixing apparatus.

2. Description of the Related Art

A liquid mixing apparatus that automatically generates a liquid mixture that is obtained by mixing a plurality of liquids at a predetermined ratio is disclosed, for example, in Patent Document 1. In general, conventional liquid mixing apparatuses include a plurality of pumps that respectively correspond to a plurality of liquids.

Further, as disclosed, for example, in Japanese Patent Application Laid-Open Publication No. 08-136451, such kind of liquid mixing apparatus is used in a chemical testing apparatus that mixes a chemical and a reagent and tests the efficacy of the chemical or, for example, in an endoscope processing apparatus that processes an endoscope using a liquid mixture in which a plurality of chemicals are mixed.

SUMMARY OF THE INVENTION

A liquid mixing apparatus of the present invention is a liquid mixing apparatus for mixing a plurality of liquids, that includes: a first tank; a first introduction section that introduces a first liquid into the first tank; a second introduction section that introduces a second liquid into the first tank; a first opening portion that is provided above a highest liquid level of the first tank; a second tank; a third introduction section that introduces a third liquid into the second tank; a second opening portion that is provided above a highest liquid level of the second tank; a liquid transfer conduit having one end arranged below a lowest liquid level in the first tank and another end connected to the second tank; an opening/closing valve that is provided in the liquid transfer conduit; a gas transfer conduit having one end arranged above the highest liquid level in the first tank and another end arranged above the highest liquid level in the second tank; a pump capable of forward/reverse operation that is provided in the gas transfer conduit and that can transfer a gas in two directions inside the gas transfer conduit; and an atmospheric release control section that controls opening and closing of the first opening portion and the second opening portion.

Further, a chemical testing apparatus of the present invention includes the liquid mixing apparatus. Furthermore, an endoscope processing apparatus of the present invention includes at least one of the liquid mixing apparatus and the chemical testing apparatus.

DETAILED DESCRIPTION OF THE PREFERRED EMBODIMENT(S)

Preferred embodiments of the present invention are described hereunder with reference to the drawings. It should be noted that the components in the drawings referred to in the following description are each displayed in a different contraction scale so as to be shown in a size that is recognizable in the drawings. Further, the present invention is not limited only to the quantity of components, the shapes of components, the ratios between the sizes of components, and the relative positional relationship between the respective components described in the drawings.

First Embodiment

Figure 1:
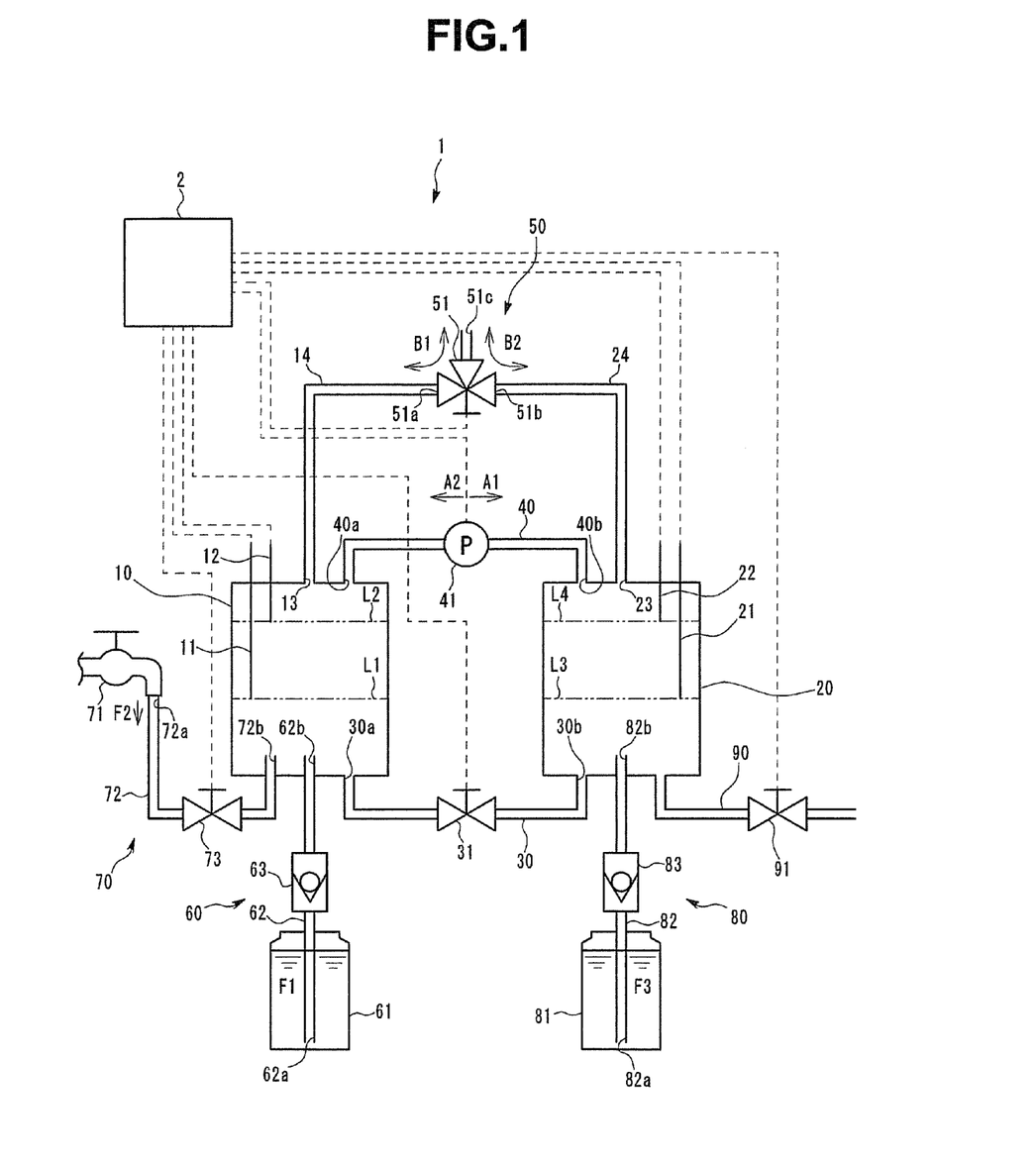
FIG. 1 is a view that illustrates a configuration of a liquid mixing apparatus according to a first embodiment.

A first embodiment of the present invention is described below. A liquid mixing apparatus 1 according to the present embodiment that is shown in FIG. 1 is, briefly, an apparatus for generating a liquid mixture in which a plurality of liquids are mixed at a predetermined ratio.

As one example according to the present embodiment it is assumed that a plurality of liquids is three kinds of liquids that include a first liquid F1, a second liquid F2, and a third liquid F3, and that the liquid mixing apparatus 1 generates a liquid mixture by mixing the first liquid F1, the second liquid F2, and the third liquid F3 at a predetermined volume ratio. Further, it is assumed that the volume ratio between the first liquid F1, the second liquid F2, and the third liquid F3 in the liquid mixture is VF1:VF2:VF3. Furthermore, as one example according to the present embodiment, as described in detail later, it is assumed that the first liquid F1, the second liquid F2, and the third liquid F3 are taken into the liquid mixing apparatus 1 through a first introduction section 60, a second introduction section 70, and a third introduction section 80, respectively.

The respective kinds of the plurality of liquids that constitute the liquid mixture and the mixing ratio of the plurality of liquids are not particularly limited. Further, the form of supplying the plurality of liquids to the liquid mixing apparatus 1 is not particularly limited and may be appropriately decided according to the circumstances. For example, the plurality of liquids may be supplied at a predetermined pressure from supply equipment that is provided outside the liquid mixing apparatus 1, or may be supplied from a storage tank or the like that is provided in the liquid mixing apparatus 1.

The liquid mixing apparatus 1 includes a first tank 10 and a second tank 20 as a pair of containers, and generates a liquid mixture by mixing the first liquid F1, the second liquid F2, and the third liquid F3 at a predetermined volume ratio inside the second tank 20. The liquid mixing apparatus 1 also includes a control section 2, the first introduction section 60, the second introduction section 70, the third introduction section 80, a liquid transfer conduit 30, an opening/closing valve 31, a gas transfer conduit 40, a pump 41, and an atmospheric release control section 50.

The control section 2 is an apparatus that controls operations of each component of the liquid mixing apparatus 1, which are described later, based on a predetermined program. For example, the control section 2 is constituted by a computer that includes a calculation apparatus, a storage apparatus, an input/output apparatus and the like.

The first tank 10 is a container that has a closed inner space of a predetermined capacity, and is configured to be capable of storing a liquid in the inner space. A first liquid level sensor 11, a second liquid level sensor 12, and a first opening portion 13 are provided in the first tank 10. The first introduction section 60, the second introduction section 70, the liquid transfer conduit 30, the gas transfer conduit 40, and the atmospheric release control section 50, that are described later, are connected to the first tank 10.

The first liquid level sensor 11 and the second liquid level sensor are components for detecting the volume of a liquid that is stored in the first tank 10. The form of the first liquid level sensor 11 and the second liquid level sensor 12 is not particularly limited as long as the first liquid level sensor 11 and the second liquid level sensor 12 are capable of detecting the volume of a liquid that is stored in the first tank 10.

As one example according to the present embodiment, the first liquid level sensor 11 and the second liquid level sensor 12 have a form that detects the volume of a liquid that is stored in the first tank 10 by measuring a liquid level (height of a liquid surface) of the liquid stored in the first tank 10.

More specifically, the first liquid level sensor 11 of the present embodiment detects whether or not the liquid level inside the first tank 10 reaches a predetermined first liquid level L1. Further, the second liquid level sensor 12 detects whether or not the liquid level inside the first tank 10 reaches a predetermined second liquid level L2 that is higher than the first liquid level L1.

The first liquid level sensor 11 and the second liquid level sensor 12 have a configuration that measures a liquid level by, for example, detecting an electrical conduction between a reference electrode that is provided in a bottom surface portion of the first tank 10 and electrodes that are arranged at the first liquid level L1 and the second liquid level L2, respectively.

In this case, the term "first liquid level L1" refers to the height of a liquid surface when a liquid of a predetermined volume V1 is stored in the first tank 10. Further, the term "second liquid level L2" refers to the height of a liquid surface when a liquid of a predetermined volume V2 that is greater than the predetermined volume V1 is stored in the first tank 10.

According to the present embodiment, a ratio of the predetermined volume V1 to a difference between the predetermined volume V2 and the predetermined volume V1 is equal to the volume ratio between the first liquid F1 and the second liquid F2 in the liquid mixture. That is, the relationship that $V1:(V2-V1)=VF1:VF2$ holds true. In this connection, a stored liquid detection sensor for detecting whether or not a liquid exists inside the first tank 10 may be arranged in the first tank 10.

The first opening portion 13 is an opening portion through which an inner space of the first tank 10 and an outer space of the first tank 10 that is at atmospheric pressure communicate. The first opening portion 13 is provided above the highest liquid level of the first tank 10. More specifically, according to the present embodiment, the first opening portion 13 is provided above the second liquid level L2. The first opening portion 13 is connected to the atmospheric release control section 50, described later, through a conduit 14.

The second tank 20 is a container that has a closed inner space of a predetermined capacity, and is configured to be capable of storing a liquid in the inner space. A third liquid level sensor 21, a fourth liquid level sensor 22, a second opening portion 23, and a discharge conduit 90 are provided in the second tank 20. The third introduction section 80, the liquid transfer conduit 30, the gas transfer conduit 40, and the atmospheric release control section 50, that are described later, are connected to the second tank 20.

The third liquid level sensor 21 and the fourth liquid level sensor 22 are components for detecting the volume of a liquid that is stored in the second tank 20. The form of the third liquid level sensor 21 and the fourth liquid level sensor 22 is not particularly limited as long as the third liquid level sensor 21 and the fourth liquid level sensor 22 are capable of detecting the volume of a liquid that is stored in the second tank 20.

As one example according to the present embodiment, the third liquid level sensor 21 and the fourth liquid level sensor 22 have a form that detects the volume of a liquid that is stored in the second tank 20 by measuring a level of the liquid stored in the second tank 20.

More specifically, the third liquid level sensor 21 of the present embodiment detects whether or not the liquid level inside the second tank 20 reaches a predetermined third liquid level L3. Further, the fourth liquid level sensor 22 detects whether or not the liquid level inside the second tank 20 reaches a predetermined fourth liquid level L4 that is higher than the third liquid level.

The third liquid level sensor 21 and the fourth liquid level sensor 22 have a configuration that measures a liquid level by, for example, detecting an electrical conduction between a reference electrode that is provided in a bottom surface portion of the second tank 20 and electrodes that are arranged at the third liquid level L3 and the fourth liquid level L4, respectively.

In this case, the term "third liquid level L3" refers to the height of a liquid surface when a liquid of a predetermined volume V3 is stored in the second tank 20. The predetermined volume V3 is less than the aforementioned predetermined volume V2. The term "fourth liquid level L4" refers to a height of the liquid surface when a liquid of a predetermined volume V4 that is greater than the predetermined volume V3 is stored in the second tank 20.

According to the present embodiment, a ratio of the predetermined volume V3 to a difference between the predetermined volume V4 and the predetermined volume V3 is equal to a ratio between the sum of the volumes of the first liquid F1 and the second liquid F2 in the liquid mixture and the volume of the third liquid F3. That is, the relationship that $V3:(V4-V3)=(VF1+VF2):VF3$ holds true. In this connection, a stored liquid detection sensor for detecting whether or not a liquid exists inside the second tank 20 may be arranged in the second tank 20.

The second opening portion 23 is an opening portion through which an inner space of the second tank 20 and an outer space of the second tank 20 that is at atmospheric pressure communicate. The second opening portion 23 is provided above the highest liquid level of the second tank 20. More specifically, according to the present embodiment, the second opening portion 23 is provided above the fourth liquid level L4. The second opening portion 23 is connected to the atmospheric release control section 50, described later, through a conduit 24.

Furthermore, according to the present embodiment, the discharge conduit 90 for discharging a liquid that is inside the second tank 20 to outside of the second tank 20 is provided in the second tank 20. The discharge conduit 20 is provided so that one end thereof opens at a bottom surface of the second tank 20. A discharge valve 91 that is an electromagnetic valve for opening and closing the discharge transfer conduit 90 is provided in the discharge conduit 20. The discharge valve 91 is electrically connected to the control section 2, and operation of the discharge valve 91 is controlled by the control section 2. According to the present embodiment, a liquid that is inside the second tank 20 can be discharged to outside the second tank 20 via the discharge conduit 90 by placing the discharge valve 91 in an open state.

The first introduction section 60 is a component for introducing the first liquid F1 into the first tank 10. As one example according to the present embodiment, the first liquid F1 is stored in a first liquid supply section 61, and the first introduction section 60 includes a first liquid introduction conduit 62 and a first liquid introduction valve 63.

The first liquid supply section 61 is a container that stores the first liquid F1. The first liquid supply section 61 has a capacity that is greater than a volume of liquid that fills the inside of the first tank 10 as far as the first liquid level L1. In this connection, a configuration may be adopted in which the first liquid supply section 61 is arranged in the liquid mixing apparatus 1, or in which the first liquid supply section 61 is provided as a separate member to the liquid mixing apparatus 1.

The first liquid introduction conduit 62 is a conduit that connects the first liquid supply section 61 and the first tank 10. One end 62a of the first liquid introduction conduit 62 is connected to the first liquid supply section 61, and another end 62b thereof is connected to the first tank 10.

The one end 62a of the first liquid introduction conduit 62 is arranged below a lowest liquid level of the first liquid supply section 61. Further, according to the present embodiment, the other end 62b of the first liquid introduction conduit 62 is arranged below the first liquid level L1 of the first tank 10.

The first liquid introduction valve 63 is arranged in the first liquid introduction conduit 62. According to the present embodiment, the first liquid introduction valve 63 has a form referred to as a so-called "check valve" that restricts the direction in which a fluid flows inside the first liquid introduction conduit 62 to only one direction. The first liquid introduction valve 63 allows a fluid to flow from the one end 62a side towards the other end 62b side inside the first liquid introduction conduit 62, and blocks the flow of a fluid from the other end 62b side towards the one end 62a side.

More specifically, according to the present embodiment, although it is possible for a fluid inside the first liquid supply section 61 to flow into the first tank 10 through the first introduction section 60, it is not possible for a fluid inside the first tank 10 to flow to the first liquid supply section 61 through the first introduction section 60.

In this connection, the first liquid supply section 61 may have a form that feeds the first liquid F1 at a predetermined pressure by means of, for example, the force of gravity or a pump. When the first liquid supply section 61 has a form that feeds the first liquid F1 at a predetermined pressure, an electromagnetic valve which can be controlled to open and close by the control section 2 serves as the first liquid introduction valve 63.

The second introduction section 70 is a component for introducing the second liquid F2 into the first tank 10. As one example according to the present embodiment, the second liquid F2 is fed at a predetermined pressure from a second liquid supply section 71. As the configuration of the second liquid supply section 71 that feeds a liquid at a predetermined pressure in this manner, for example, water supply equipment or a liquid feeding apparatus that includes a pump or the like may be considered. Note that the second liquid supply section 71 may have a container-like form that stores the second liquid F2.

The second introduction section 70 includes a second liquid introduction conduit 72 and a second liquid introduction valve 73. The second liquid introduction conduit 72 connects the second liquid supply section 71 and the first tank 10. One end 72a of the second liquid introduction conduit 72 is connected to the second liquid supply section 71, and another end 72b thereof is connected to the first tank 10.

According to the present embodiment, the other end 72b of the second liquid introduction conduit 72 is arranged below the first liquid level L1 of the first tank 10, and preferably is arranged at the bottom surface portion of the first tank 10. By arranging the other end 72b of the second liquid introduction conduit 72 below the first liquid level L1 of the first tank 10 in this manner, a liquid that is stored inside the first tank 10 can be agitated by the flow of the second liquid F2 that is introduced into the first tank 10 from the other end 72b of the second liquid introduction conduit 72.

The second liquid introduction valve 73 is arranged in the second liquid introduction conduit 72. The second liquid introduction valve 73 is an electromagnetic valve for opening and closing the second liquid introduction conduit 72. The second liquid introduction valve 73 is electrically connected to the control section 2. Operation of the second liquid introduction valve 73 is controlled by the control section 2.

The third introduction section 80 is a component for introducing the third liquid F3 into the second tank 20. As one example according to the present embodiment, the third liquid F3 is stored in a third liquid supply section 81, and the third introduction section 80 includes a third liquid introduction conduit 82 and a third liquid introduction valve 83.

The third liquid supply section 81 is a container that stores the third liquid F3. The third liquid supply section 81 has a capacity that is greater than a volume of liquid that fills the inside of the second tank 20 as far as the fourth liquid level L4 from the third liquid level L3. In this connection, the third liquid supply section 81 may be arranged in the liquid mixing apparatus 1, or may be provided as a separate member to the liquid mixing apparatus 1.

The third liquid introduction conduit 82 is a conduit that connects the third liquid supply section 81 and the second tank 20. One end 82a of the third liquid introduction conduit 82 is connected to the third liquid supply section 81, and another end 82b thereof is connected to the second tank 20.

The one end 82a of the third liquid introduction conduit 82 is arranged below a lowest liquid level of the third liquid supply section 81. According to the present embodiment, the other end 82b of the third liquid introduction conduit 82 is arranged below the third liquid level L3 of the second tank 20.

By arranging the other end 82b of the third liquid introduction conduit 82 below the third liquid level L3 of the second tank 20 in this manner, a liquid that is stored inside the second tank 20 can be agitated by the flow of the third liquid F3 that is introduced into the second tank 20 from the other end 82b of the third liquid introduction conduit 82.

The third liquid introduction valve 83 is arranged in the third liquid introduction conduit 82. According to the present embodiment, similarly to the first liquid introduction valve 63, the third liquid introduction valve 83 has a form referred to as a so-called "check valve". The third liquid introduction valve 83 allows a fluid to flow from the one end 82a side towards the other end 82b side inside the second liquid introduction conduit 82, and blocks the flow of a fluid from the other end 82b side towards the one end 82a side.

More specifically, according to the present embodiment, although it is possible for a fluid inside the third liquid supply section 81 to flow into the second tank 20 through the third introduction section 80, it is not possible for a fluid inside the second tank 20 to flow to the third liquid supply section 81 through the third introduction section 80.

In this connection, the third liquid supply section 81 may have a form that feeds the third liquid F3 at a predetermined pressure by means of, for example, the force of gravity or a pump. When the third liquid supply section 81 has a form that feeds the third liquid F3 at a predetermined pressure, an electromagnetic valve which can be controlled to open and close by the control section 2 serves as the third liquid introduction valve 83.

The liquid transfer conduit 30 is a conduit that connects the first tank 10 and the second tank 20. One end 30a of the liquid transfer conduit 30 is arranged below the lowest liquid level inside the first tank 10, and another end 30b of the liquid transfer conduit 30 is arranged inside the second tank 20.

More specifically, according to the present embodiment, the lowest liquid level of the first tank 10 is the bottom surface of the first tank 10, and the one end 30a of the liquid transfer conduit 30 is provided so as to open at the bottom surface of the first tank 10. In this connection, when a pressure inside the liquid transfer conduit 30 is made a more negative pressure than a pressure inside the first tank 10, it is sufficient to arrange the one end 30a of the liquid transfer conduit 30 so that it is possible to suck all the liquid stored in the first tank 10 into the liquid transfer conduit 30. For example, a form may be adopted in which the one end 30a of the liquid transfer conduit 30 is arranged facing the bottom surface of the first tank 10 so as to suck up liquid from the bottom surface of the first tank 10 into the liquid transfer conduit 30.

According to the present embodiment, the other end 30b of the liquid transfer conduit 30 is provided so as to open at the bottom surface of the second tank 20. In this connection, it is sufficient that the other end 30b of the liquid transfer conduit 30 is of a form that enables liquid inside the liquid transfer conduit 30 to flow into the second tank 20, and the form thereof is not limited to that of the present embodiment.

The opening/closing valve 31 is provided in the liquid transfer conduit 30. The opening/closing valve 31 is an electromagnetic valve for opening and closing the liquid transfer conduit 30. The opening/closing valve 31 is electrically connected to the control section 2. Operation of the opening/closing valve 31 is controlled by the control section 2.

The gas transfer conduit 40 is a conduit that connects the first tank 10 and the second tank 20. One end 40a of the gas transfer conduit 40 is arranged above the highest liquid level inside the first tank 10. Another end 40b of the gas transfer conduit 40 is arranged above the highest liquid level inside the second tank 20.

More specifically, according to the present embodiment, the one end 40a of the gas transfer conduit 40 is provided above the second liquid level L2 of the first tank 10. Further, the other end 40b of the gas transfer conduit 40 is provided above the fourth liquid level L4 of the second tank 20.

The pump 41 is arranged in the gas transfer conduit 40. The pump 41 is an apparatus that transfers a gas inside the gas transfer conduit 40. The pump 41 can be run to operate in a forward direction to transfer a gas from the one end 40a side towards the other end 40b side (as indicated by an arrow A1 in FIG. 1), or to operate in a reverse direction to transfer a gas from the other end 40b side towards the one end 40a side (indicated by an arrow A2 in FIG. 1).

The pump 41 of this kind that is configured to be capable of transferring a gas in two directions inside the gas transfer conduit 40 is generally referred to as a "pump capable of forward/reverse operation". The form of the pump 41 capable of forward/reverse operation is not particularly limited and, for example, a form that is referred to as a "tube pump" can be applied. The pump 41 is electrically connected to the control section 2. The operation of the pump 41 is controlled by the control section 2.

The atmospheric release control section 50 is a component for controlling opening and closing of the first opening portion 13 of the first tank 10 and the second opening portion 23 of the second tank 20. In other words, the atmospheric release control section 50 is a component for controlling whether to open the respective inner spaces of the first tank 10 and the second tank 20 to the apparatus atmosphere to make the pressure in the inner spaces the atmospheric pressure (to place the inner spaces in an atmospheric release state) or to place the inner spaces in an airtight state.

In the liquid mixing apparatus 1 according to the present invention, it is not essential that the atmospheric release control section 50 control opening and closing of the first tank 10 and the second tank 20 in an independent manner, as long as at least a configuration such that, when one of the first tank 10 and the second tank 20 is placed in an atmospheric release state, the atmospheric release control section 50 is capable of placing the other of the first tank 10 and the second tank 20 in an airtight state, is adopted.

Although the form of the atmospheric release control section 50 is not particularly limited, as one example according to the present embodiment the atmospheric release control section 50 is constituted by a three-way valve 51. The three-way valve 51 includes a first port 51a that is connected to the first opening portion 13 through the conduit 14, a second port 51b that is connected to the second opening portion 23 through the conduit 24, and an atmospheric release port 51c that is open to the apparatus atmosphere.

The three-way valve 51 has a configuration which enables selection of either one of a state in which the first port 51a and the atmospheric release port 51c communicate and the second port 52b is blocked (indicated by an arrow B1 in FIG. 1), and a state in which the second port 51b and the atmospheric release port 51c communicate and the first port 51a is blocked (indicated by an arrow B2 in FIG. 1). The three-way valve 51 is electrically connected to the control section 2, and operation of the three-way valve 51 is controlled by the control section 2.

In this connection, although the atmospheric release control section 50 of the present embodiment is constituted by the three-way valve 51, the atmospheric pressure release control section 50 may be constituted, for example, by a pair of electromagnetic valves that are provided in the first opening portion 13 and the second opening portion 23, respectively. However, by adopting a configuration in which the atmospheric release control section 50 is constituted by the three-way valve 51 as in the present embodiment as illustrated in FIG. 1, in comparison to a configuration that uses a pair of electromagnetic valves, the number of components of the atmospheric release control section 50 can be reduced and the atmospheric release control section 50 can be miniaturized.

A filter for filtering a gas that passes through the atmospheric release port 51c may also be provided in the atmospheric release port 51c of the three-way valve 51. The filter may have a configuration that includes activated carbon. By including activated carbon in the filter, gases released to the atmosphere from the first tank 10 and the second tank 20 can be deodorized.

Operations to generate a liquid mixture that are performed by the liquid mixing apparatus 1 of the present embodiment having the above described configuration are described hereafter. The operations described below are performed in accordance with a predetermined program that is stored in the control section 2.

First, an initialization process is performed before beginning generation of a liquid mixture. In the initialization process, the second liquid introduction valve 73, the opening/closing valve 31, and the discharge valve 91 are placed in a closed state, and the pump 41 is placed in a stopped state.

In this connection, if a stored liquid detection sensor is arranged in each of the first tank 10 and the second tank 20, it is preferable to perform the following processes after confirming that there is no liquid inside the first tank 10 and the second tank 20 by means of the stored liquid detection sensors.

Figure 2:
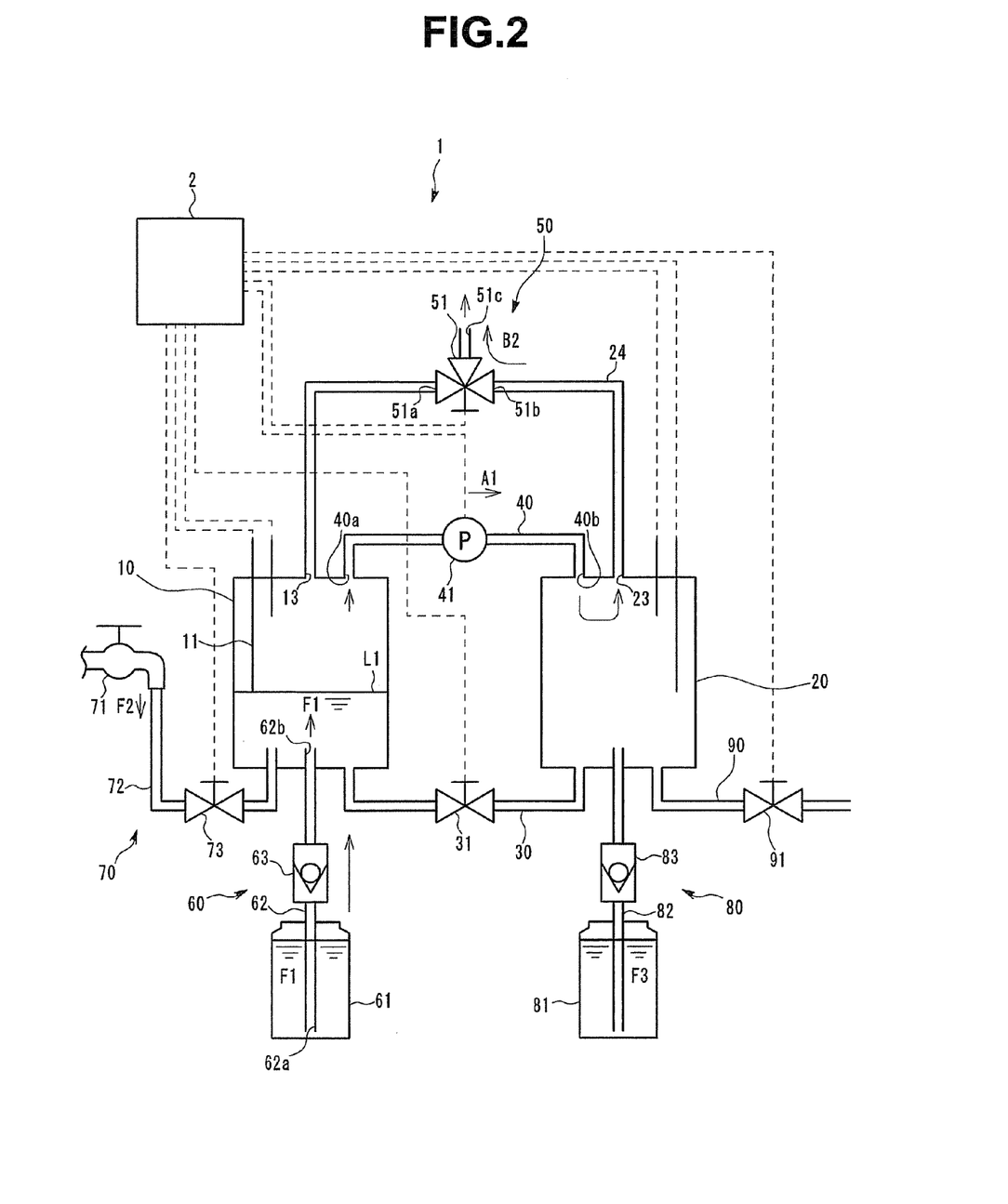
FIG. 2 is a view that describes a first liquid introduction process of the liquid mixing apparatus.

Next, a first liquid introduction process is performed that introduces the first liquid F1 into the first tank 10 until the first liquid F1 reaches the first liquid level L1. According to the first liquid introduction process, as shown in FIG. 2, the three-way valve 51 of the atmospheric release control section 50 is placed in a state in which the second port 51b and the atmospheric release port 51c communicate and the first port 51a is blocked. More specifically, the second opening portion 23 is placed in an open state and the inner space of the second tank 20 is opened to the atmosphere. The pump 41 is then placed in a forward direction operation state.

Thus, as a result of the pump 41 performing a forward direction operation, the pressure inside the first tank 10 becomes a negative pressure (state in which the air pressure is lower than the atmospheric pressure), and hence the first liquid F1 inside the first liquid supply section 61 is sucked up and introduced into the first tank 10 from the first introduction section 60. When the first liquid level sensor 11 detects that the liquid level in the first tank 10 has reached the first liquid level L1, the operation of the pump 41 is stopped. Thus, the first liquid F1 of the predetermined volume V1 is stored in the first tank 10 by performing the above described first liquid introduction process.

Figure 3:
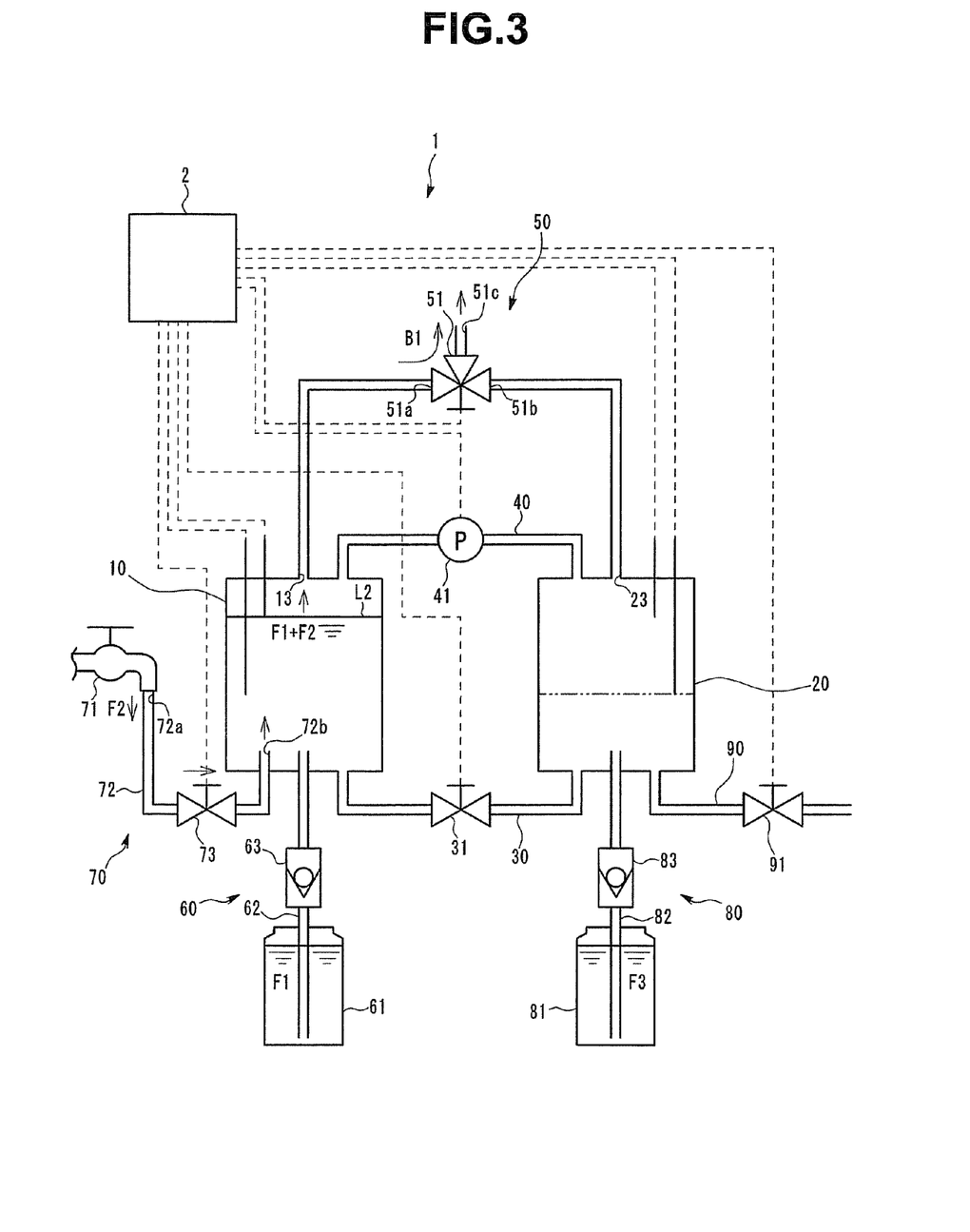
FIG. 3 is a view that describes a second liquid introduction process of the liquid mixing apparatus.

Next, a second liquid introduction process is performed that introduces the second liquid F2 into the first tank 10 until the second liquid F2 reaches the second liquid level L2. In the second liquid introduction process, as shown in FIG. 3, the three-way valve 51 of the atmospheric release control section 50 is placed in a state in which the first port 51a and the atmospheric release port 51c communicate and the second port 51b is blocked. More specifically, the first opening portion 13 is placed in an open state and the inner space of the first tank 10 is opened to the atmosphere. The second liquid introduction valve 63 is then placed in an open state.

Thus, since the second liquid F2 is being supplied at a predetermined pressure from the second liquid supply section 71, the second liquid F2 is introduced into the first tank 10 from the second introduction section 70. At this time, because the first liquid introduction valve 63 is a check valve, the fluid inside the first tank 10 does not flow back to the first liquid supply section 61.

When the second liquid level sensor 12 detects that the liquid level in the first tank 10 has reached the second liquid level L2, the second liquid introduction valve 73 is placed in a closed state. By means of the above described second liquid introduction process, a preliminary liquid mixture of the predetermined volume V2 for which a volume ratio between the first liquid F1 and the second liquid F2 is VF1:VF2 is stored.

Note that, according to the second liquid introduction process, because the second liquid F2 is supplied at a predetermined pressure from the second liquid supply section 71, even if the inner space of the first tank 10 is in an airtight state and is not open to the atmosphere, the second liquid F2 can be introduced into the first tank 10.

Figure 4:
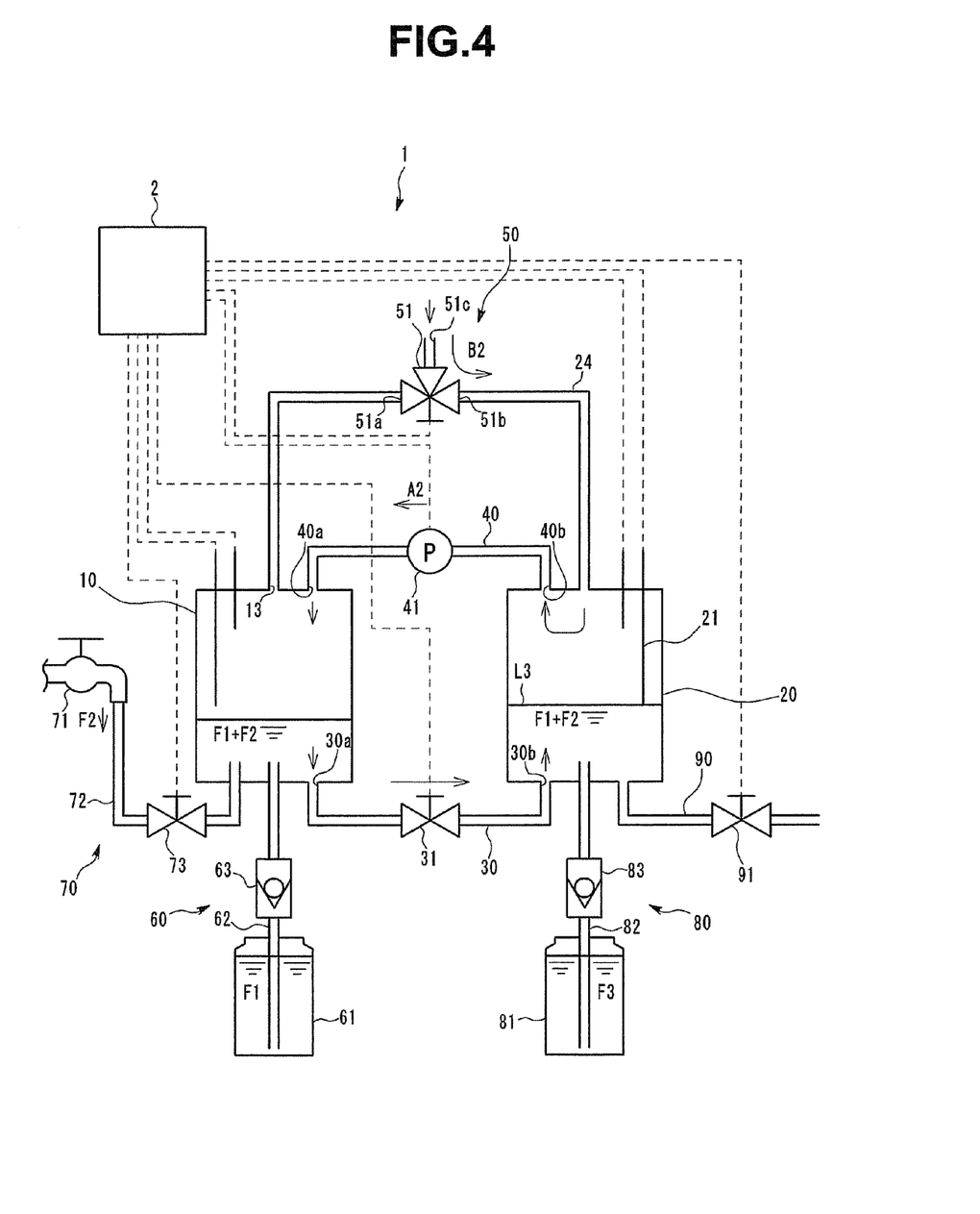
FIG. 4 is a view that describes a transfer process of the liquid mixing apparatus.

Next, a transfer process is performed that transfers the preliminary liquid mixture that is inside the first tank 10 into the second tank 20 until the liquid mixture in the second tank 20 reaches the third liquid level L3. According to the transfer process, as shown in FIG. 4, the three-way valve 51 of the atmospheric release control section 50 is placed in a state in which the second port 51b and the atmospheric release port 51c communicate and the first port 51a is blocked. More specifically, the second opening portion 23 is placed in an open state and the inner space of the second tank 20 is opened to the atmosphere. The pump 41 is then placed in a reverse direction operation state, and the opening/closing valve 31 is placed in an open state.

Thus, because the inside of the first tank 10 in which the first opening portion 13 has been placed in a closed state becomes a positive pressure (state in which the air pressure is higher than the atmospheric pressure) as a result of the reverse direction operation performed by the pump 41, the preliminary liquid mixture is transferred into the second tank 20 through the liquid transfer conduit 30 in a manner in which the preliminary liquid mixture is pushed out from inside the first tank 10. At this time, because the inner space of the second tank 20 is open to the atmosphere, a situation does not occur in which the third liquid F3 inside the second liquid supply section 81 is sucked up and flows into the second tank 20.

When the third liquid level sensor 21 detects that the liquid level in the second tank 20 has reached the third liquid level L3, the opening/closing valve 31 is placed in a closed state and operation of the pump 41 is stopped. By means of the aforementioned transfer process, a preliminary liquid mixture of the predetermined volume V3 is stored in the second tank 20.

Note that if the third liquid introduction valve 83 is an electromagnetic valve, besides the above described form of carrying out the transfer process, the transfer process may also be carried out by opening the inner space of the first tank 10 to the atmosphere and placing the second opening portion 23 of the second tank 20 in a closed state, and then operating the pump 41 in the reverse direction. In this case, since the inside of the second tank 20 becomes a negative pressure as a result of the reverse direction operation of the pump 41, the preliminary liquid mixture is transferred from the first tank 10 by being sucked into the second tank 20.

Figure 5:
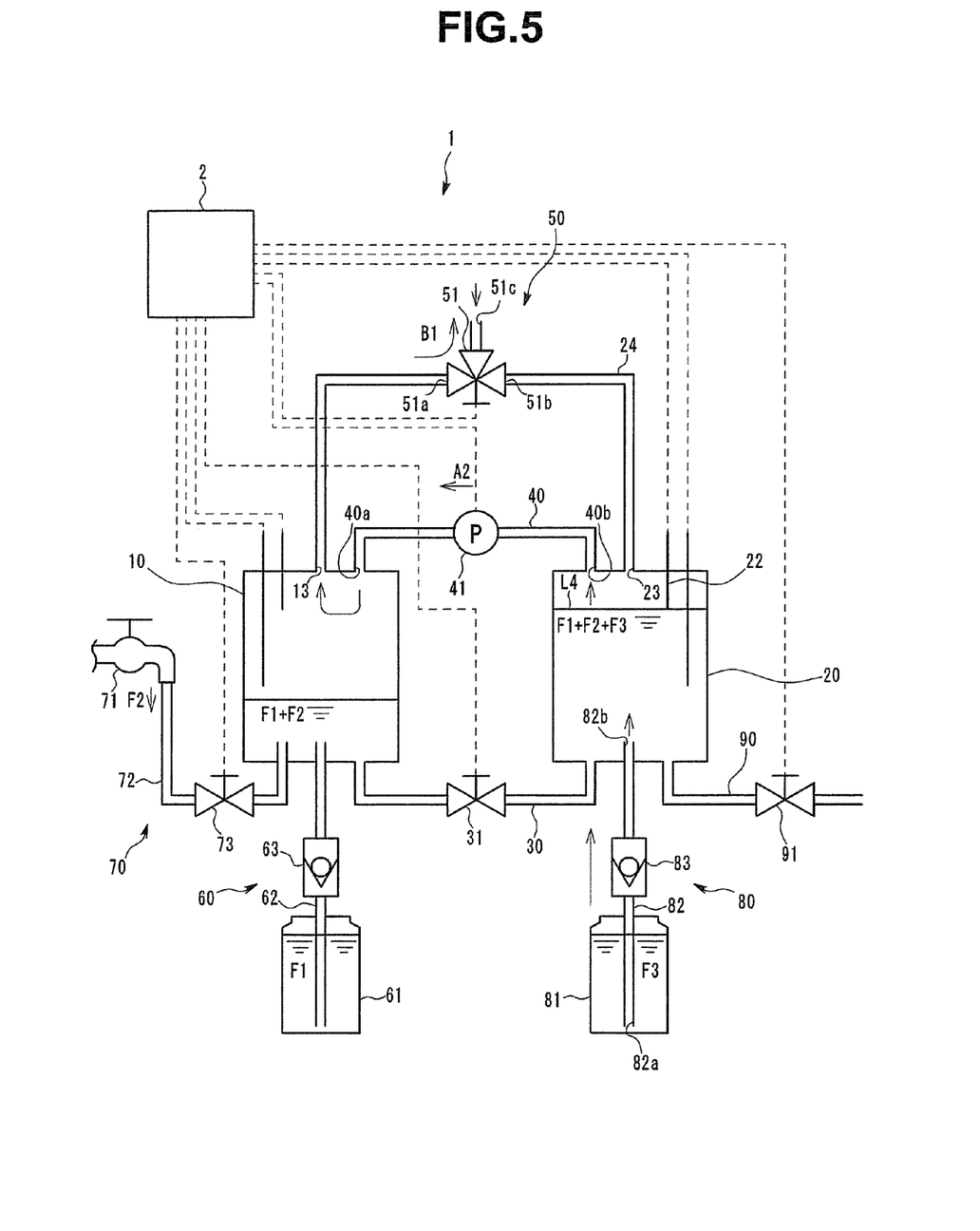
FIG. 5 is a view that describes a third liquid introduction process of the liquid mixing apparatus.

Next, a third liquid introduction process is performed that introduces the third liquid F3 into the second tank 20 up to the fourth liquid level L4. In the third liquid introduction process, as shown in FIG. 5, the three-way valve 51 of the atmospheric release control section 50 is placed in a state in which the first port 51a and the atmospheric release port 51c communicate and the second port 51b is blocked. More specifically, the first opening portion 13 is placed in an open state and the inner space of the first tank 10 is opened to the atmosphere. The pump 41 is then placed in a reverse direction operation state.

Thus, because the inside of the second tank 20 becomes a negative pressure as a result of the reverse direction operation performed by the pump 41, the third liquid F3 that is inside the third liquid supply section 81 is sucked upward and is introduced into the second tank 20 from the third introduction section 80.

Subsequently, when the fourth liquid level sensor 22 detects that the liquid level inside the second tank 20 has reached the fourth liquid level L4, the operation of the pump 41 is stopped. By means of the above described third liquid introduction process, a liquid mixture of the predetermined volume V4 for which a volume ratio between the first liquid F1, the second liquid F2, and the third liquid F3 is VF1:VF2:VF3 is stored in the second tank 20.

By carrying out the above described operations, the liquid mixing apparatus 1 of the present embodiment generates a liquid mixture in which the volume ratio between the first liquid F1, the second liquid F2, and the third liquid F3 is VF1:VF2:VF3.

When discharging the liquid mixture that is stored inside the second tank 20 to outside the liquid mixing apparatus 1, a discharge process that is described next is performed. In the discharge process, the three-way valve 51 of the atmospheric release control section 50 is placed in a state in which the first port 51*a* and the atmospheric release port 51*c* communicate and the second port 51*b* is blocked. More specifically, the first opening portion 13 is placed in an open state and the inner space of the first tank 10 is opened to the atmosphere. Further, the pump 41 is placed in a forward direction operation state and the discharge valve 91 is placed in an open state.

Thus, because the pressure inside the second tank 20 in which the second opening portion 23 has been placed in a closed state becomes a positive pressure as the result of the forward direction operation performed by the pump 41, the liquid mixture is discharged through the discharge conduit 90 in a manner in which the liquid mixture is pushed out from inside the second tank 20.

Note that the form in which a liquid mixture is discharged to outside the liquid mixing apparatus 1 is not limited to the aforementioned embodiment. For example, a configuration may be adopted in which the liquid mixture is discharged using the force of gravity by opening the inner space of the second tank 20 to the atmosphere and placing the discharge valve 91 in an open state.

When all of the liquid mixture has been discharged from inside the second tank 20 by the discharge process, the preliminary liquid mixture remains inside the first tank 10 in the liquid mixing apparatus 1. In order to discharge the preliminary liquid mixture that remains in the first tank 10 to outside the liquid mixing apparatus 1, it is sufficient to transfer the preliminary liquid mixture in the first tank 10 to the second tank 20 in the same manner as in the above described transfer process, and thereafter perform the aforementioned discharge process. Note that if the volume of the preliminary liquid mixture that remains is greater than a volume that fills the second tank 20 up to the highest liquid level (fourth liquid level L4 according to the present embodiment), it is sufficient to repeat the transfer process and discharge process operations.

As described above, with a simple configuration that includes only one pump 41 capable of forward/reverse operation, the liquid mixing apparatus 1 of the present embodiment can generate a liquid mixture in which the first liquid F1, the second liquid F2, and the third liquid F3 are mixed at a predetermined volume ratio.

Further, according to the liquid mixing apparatus 1 of the present embodiment, the first liquid introduction valve 63 and the third liquid introduction valve 83 can be implemented by a member referred to as a "check valve" that has a simple configuration that does not require wiring or an actuator.

In addition, according to the liquid mixing apparatus 1 of the present embodiment, the gas transfer conduit 40 connects an area above the highest liquid level of the first tank 10 and an area above the highest liquid level of the second tank 20. Therefore, gas is the only fluid that flows through the inside of the gas transfer conduit 40, and the first liquid F1, the second liquid F2, and the third liquid F3 that constitute the liquid mixture do not pass through the inside of the gas transfer conduit 40.

Accordingly, for example, even if at least one of the first liquid F1, the second liquid F2, and the third liquid F3 or the liquid mixture is a chemical that is aggressive towards metal or resin or the like, it is not necessary to take into consideration the vulnerability of the gas transfer conduit 40 or the pump 41 to the chemical. Generally, a conduit or a pump that has been manufactured while taking into consideration handling of a chemical that is aggressive towards metal or resin is more expensive than a conduit or a pump that is made without giving consideration to the handling of such a chemical. According to the present embodiment, it is possible to generate an aggressive liquid mixture with a comparatively inexpensive apparatus configuration that does not use such kind of expensive conduit or pump. Similarly, it is not necessary to take into consideration the vulnerability of the atmospheric release control section 50 and the three-way valve 51 to such a chemical.

In this connection, although according to the present embodiment illustrated in FIG. 1, the gas transfer conduit 40 connects to the first tank 10 and the second tank 20 at different positions to the atmospheric release control section 50, a configuration may be adopted in which the gas transfer conduit 40 and the atmospheric release control section 50 connect to the first tank 10 and the second tank 20 at the same positions.

Figure 6:
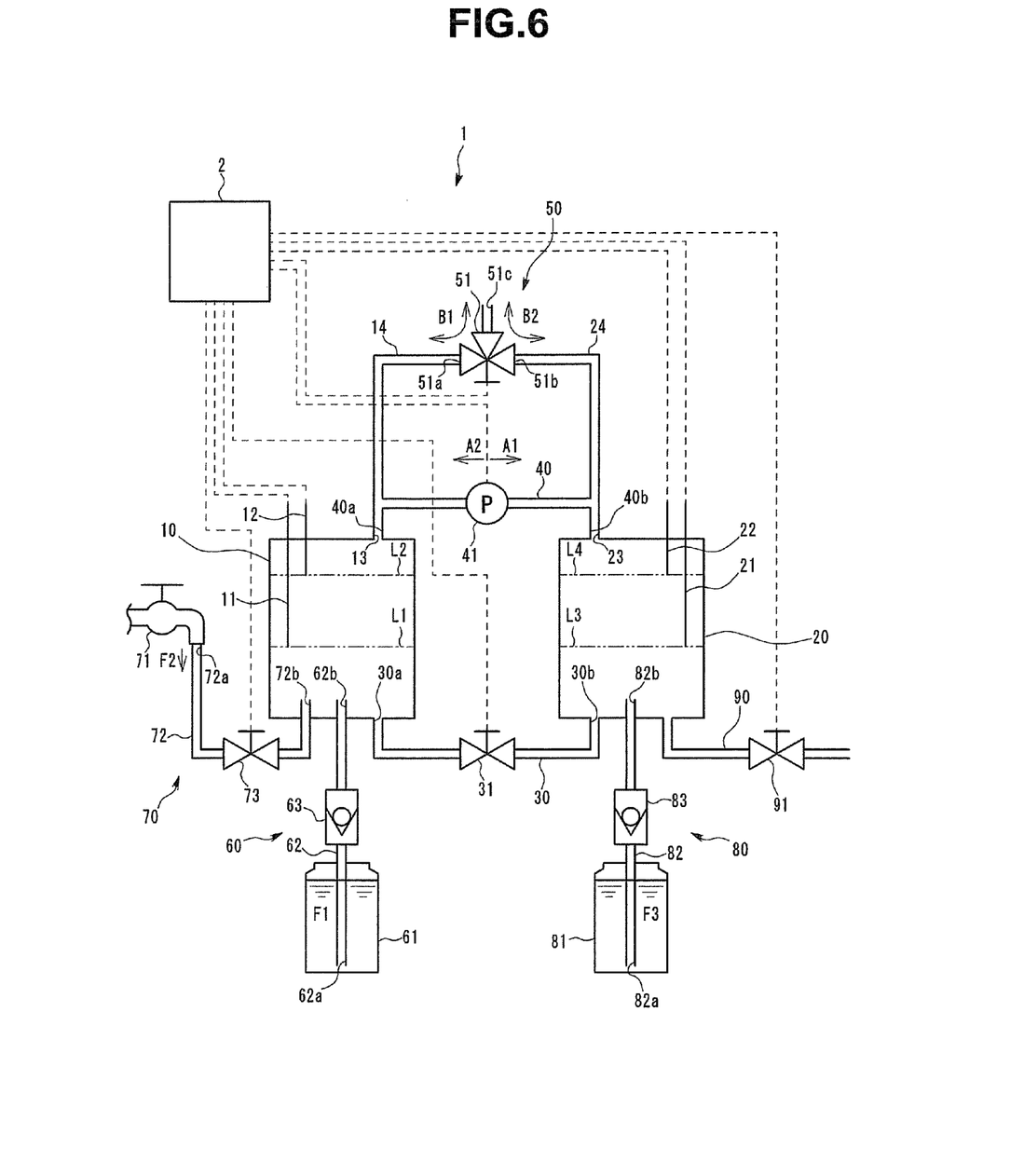
FIG. 6 is a view that describes a modification example of the first embodiment.

More specifically, as illustrated in a modification example of the present embodiment shown in FIG. 6, a configuration may be adopted in which the one end 40*a* of the gas transfer conduit 40 communicates with the first opening portion 13 of the first tank 10 and the other end 40*b* thereof communicates with the second opening portion 20 of the second tank 20.

By adopting a configuration in which the gas transfer conduit 40 and the atmospheric release control section 50 connect to the same opening portions in the first tank 10 and the second tank 20 in this manner, the first tank 10 and the second tank 20 can be made with a simpler shape that is easier to manufacture.

Second Embodiment

Figure 7:
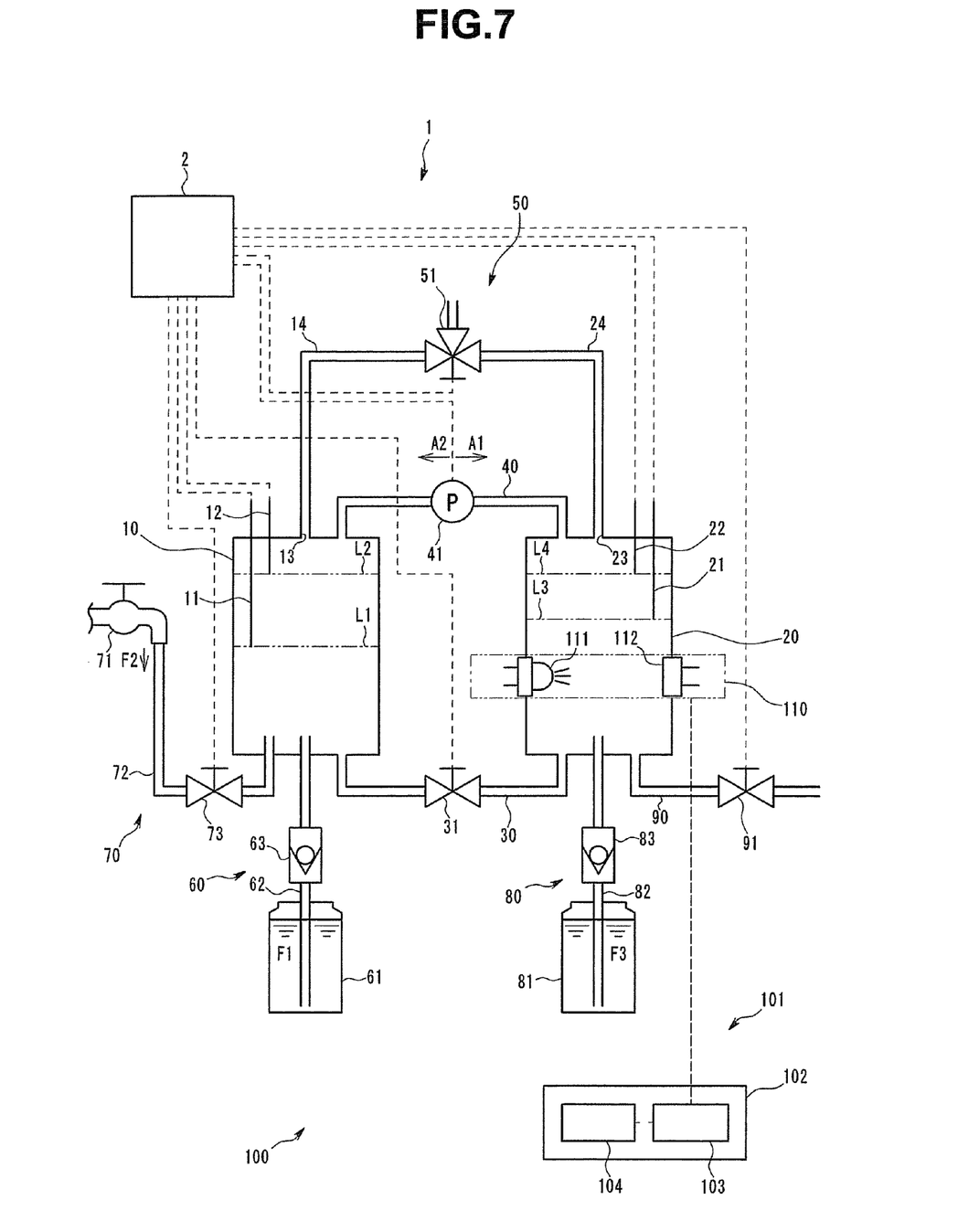
FIG. 7 is a view that describes a configuration of a chemical testing apparatus according to a second embodiment.

A second embodiment of the present invention is described hereunder referring to FIG. 7. Only the differences with respect to the first embodiment are described hereunder, and components that are the same as in the first embodiment are denoted by the same reference symbols, and a description of such components is omitted as appropriate.

A chemical testing apparatus 100 of the present embodiment includes the liquid mixing apparatus 1 and a chemical testing section 101. The chemical testing apparatus 100 is an apparatus that generates a liquid mixture in which a predetermined chemical is mixed with a reagent using the liquid mixing apparatus 1, and qualitatively or quantitatively tests the liquid mixture using the chemical testing section 101 to evaluate the efficacy of the chemical.

Although a chemical and a reagent as well as the form of testing that are used by the chemical testing apparatus 100 are not particularly limited, as one example according to the present embodiment it is assumed that the chemical is diluted with tap water and thereafter the chemical is mixed with a reagent that reacts therewith, and the efficacy of the chemical is evaluated by measuring a change in the color of the liquid mixture by means of an absorptiometer.

More specifically, after generating a preliminary liquid mixture in which the first liquid F1 that is a chemical and the second liquid F2 that is tap water are mixed at a predetermined ratio, the liquid mixing apparatus 1 of the present embodiment generates a liquid mixture in which the preliminary liquid mixture and a third liquid that is a reagent are mixed. Subsequently, the chemical testing section 101 measures the absorbance of the liquid mixture. In this connection, as a combination of a chemical, a reagent, and a testing method according to the present embodiment, for example, a combination may be mentioned that uses a reagent including a potassium iodide solution whose amount of transmitted light changes according to the concentration of a chemical, with respect to a chemical that is an antiseptic solution that includes an aqueous peracetic acid solution that is used in an endoscope disinfection process.

The configuration of the liquid mixing apparatus 1 of the present embodiment differs from that of the first embodiment in that a measuring section 110 of the chemical testing section 101 is arranged in the second tank 20 as described later. The chemical testing section 101 includes the measuring section 110 and a measurement control section 102.

According to the present embodiment, the measuring section 110 is an absorptiometer that measures an absorbance of a liquid mixture that is stored inside the second tank 20. The configuration of an absorptiometer is known, and therefore a detailed description thereof is omitted herein. The measuring section 110 includes a light emission section 111 and a light reception section 112.

The light emission section 111 emits light of a predetermined wavelength and a predetermined intensity. The light reception section 112 is arranged so as to be separated from the light emission section 111 by a predetermined distance, and measures the intensity of a light that is emitted from the light emission section 111. The measuring section 110 measures the absorbance of a liquid mixture that is present between the light emission section 111 and the light reception section 112 based on changes in the intensity of the light measured at the light reception section 111.

The measurement control section 102 includes a comparison and judgment section 103 and an outputting section 104. The comparison and judgment section 103 compares an absorbance of a liquid mixture in the second tank 20 that is measured by the measuring section 110 with a predetermined threshold value, and judges the result of the efficacy test of the chemical based on the size relationship between the two values.

The outputting section 104 outputs at least one of the judgment result obtained by the comparison and judgment section 103 and the measurement result obtained by the measuring section 110 to outside. Although the form of the output of the outputting section 104 is not particularly limited, for example, a form may be considered in which the outputting section 104 includes a light emitting apparatus or an image display apparatus or the like, and outputs the result of the efficacy test of the chemical by visually displaying the result.

The comparison and judgment section 103 may also be capable of outputting sound, and may output a result of an efficacy test of a chemical by sound. Further, the outputting section 104 may be of a form that outputs an electrical signal that changes according to a judgment result of the comparison and judgment section 103 or a measurement result of the measuring section 110 to outside. In this connection, the measurement control section 102 may be integrated with the control section 2 of the liquid mixing apparatus 1.

As described above, the chemical testing apparatus 100 that includes the liquid mixing apparatus 1 can evaluate the efficacy of a chemical (first liquid F1) stored in the first liquid supply section 61. As described above with respect to the first embodiment, because the liquid mixing apparatus 1 has a simple configuration, the chemical testing apparatus 100 of the present embodiment can also be made with a simple configuration, and it is easy to miniaturize the chemical testing apparatus 100 and reduce the manufacturing cost thereof.

Further, for example, when mixing a chemical (antiseptic solution) and a reagent and performing an absorbance measurement, although the chemical and the reagent are mixed at a predetermined ratio, when comparing the volume of the chemical with the volume of the reagent, in some cases it is necessary to significantly increase the volume of the reagent. Furthermore, in general, it is difficult to accurately measure a trace amount of a liquid.

Therefore, in order to accurately mix a chemical and a reagent whose volumes differ significantly at the time of mixing, the volume of the chemical whose volume to be used is originally small must be increased to a volume that enables accurate measurement. Consequently, the volume of the reagent that is mixed with the chemical whose volume has been increased to enable accurate measurement thereof becomes a relatively large volume, and a large quantity of the reagent is required for the efficacy test.

With respect to this problem, according to the chemical testing apparatus 100 of the present embodiment, after extracting only a volume of the first liquid F1, which is a chemical (antiseptic solution), that is required to enable accurate measurement thereof, the first liquid F1 is diluted with the second liquid F2 that is tap water, and one part of the resulting preliminary liquid mixture is mixed with the reagent that is the third liquid F3. Thus, the volume of reagent required for the efficacy test of the chemical can be decreased.

According to the present embodiment as described above, an efficacy test of a chemical can be accurately conducted by obtaining an accurate liquid mixture, and the amount of a reagent that is required for the efficacy test can also be decreased. Furthermore, since the capacity of the third liquid supply section 81 that stores a reagent can be reduced because the amount of reagent required to conduct an efficacy test of a chemical is decreased, the apparatus can be miniaturized.

Third Embodiment

Figure 8:
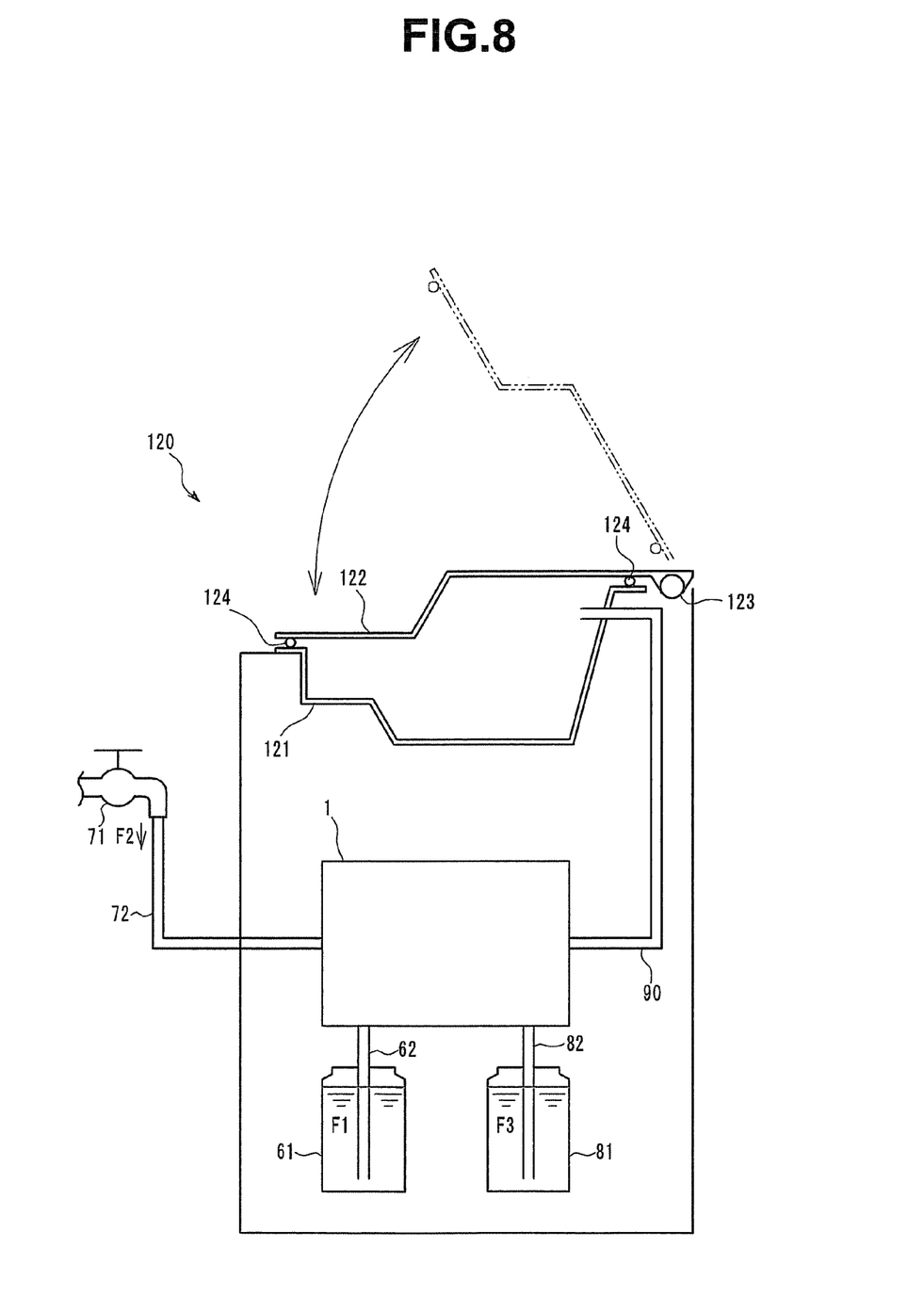
FIG. 8 is a view that describes a configuration of an endoscope processing apparatus according to a third embodiment.

A third embodiment of the present invention is described hereunder referring to FIG. 8. Only the differences with respect to the first embodiment are described hereunder, and components that are the same as in the first embodiment are denoted by the same reference symbols, and a description of such components is omitted as appropriate.

An endoscope processing apparatus 120 according to the present embodiment includes the liquid mixing apparatus 1 and a processing tank 121. The endoscope processing apparatus 120 is an apparatus that performs at least one of a cleaning process and a disinfection process using a liquid mixture that is generated by the liquid mixing apparatus 1 with respect to an unshown endoscope that is accommodated inside the processing tank 121 which is capable of accommodating the endoscope.

The kind of liquid mixture used for processing the endoscope is not particularly limited. As one example according to the present embodiment, the liquid mixture is obtained by mixing the first liquid F1 that is stored in the first liquid supply section 61 and the third liquid F3 that is stored in the second liquid supply section at a predetermined ratio, and thereafter diluting the resulting mixture at a predetermined ratio with the second liquid F2 that is tap water that is supplied from the second liquid supply section 71. The manner in which the liquid mixing apparatus can generate liquid mixture like this is described in the first embodiment.

The processing tank 121 is a tub-shaped container that is capable of storing a chemical and that has a shape that can accommodate an endoscope. The processing tank 121 is provided with a lid portion 122 that opens and closes an opening portion thereof. The lid portion 122 is supported by a hinge portion 123, and is rotatable between a closed position at which the lid portion 122 closes the opening portion of the processing tank 121 and an open position at which the lid portion 122 opens the opening portion.

Packing 124 is arranged in the processing tank 121 so as to be interposed between the lid portion 122 and the opening portion of the processing tank 121 in a state in which the lid portion 122 is at the closed position. By means of the above configuration, the opening portion of the processing tank 121 can be hermetically sealed during processing of an endoscope.

The discharge conduit 90 of the liquid mixing apparatus 1 is connected to the processing tank 121. A liquid mixture that is generated by mixing a plurality of liquids in the liquid mixing apparatus 1 is introduced into the processing tank 121 through the discharge conduit 90.

As described above, the endoscope processing apparatus 120 of the present embodiment can execute at least one of a cleaning process and a disinfection process with respect to an endoscope using a processing liquid that is obtained by mixing the first liquid F1, the second liquid F2, and a third liquid at a predetermined ratio.

According to the present embodiment, as described in the first embodiment, because the liquid mixing apparatus 1 has a simple configuration, the endoscope processing apparatus 120 of the present embodiment can also be made with a simple configuration, and it is easy to miniaturize the endoscope processing apparatus 120 and decrease the manufacturing cost thereof.

Further, according to the present embodiment, a liquid mixture that is generated by the liquid mixing apparatus 1 can be transferred into the processing tank 121 using the pump 41 of the liquid mixing apparatus 1. It is therefore possible to reduce the number of pumps included in the endoscope processing apparatus 120. It is thereby easier to miniaturize the endoscope processing apparatus 120 and decrease the manufacturing cost thereof.

Fourth Embodiment

Figure 9:
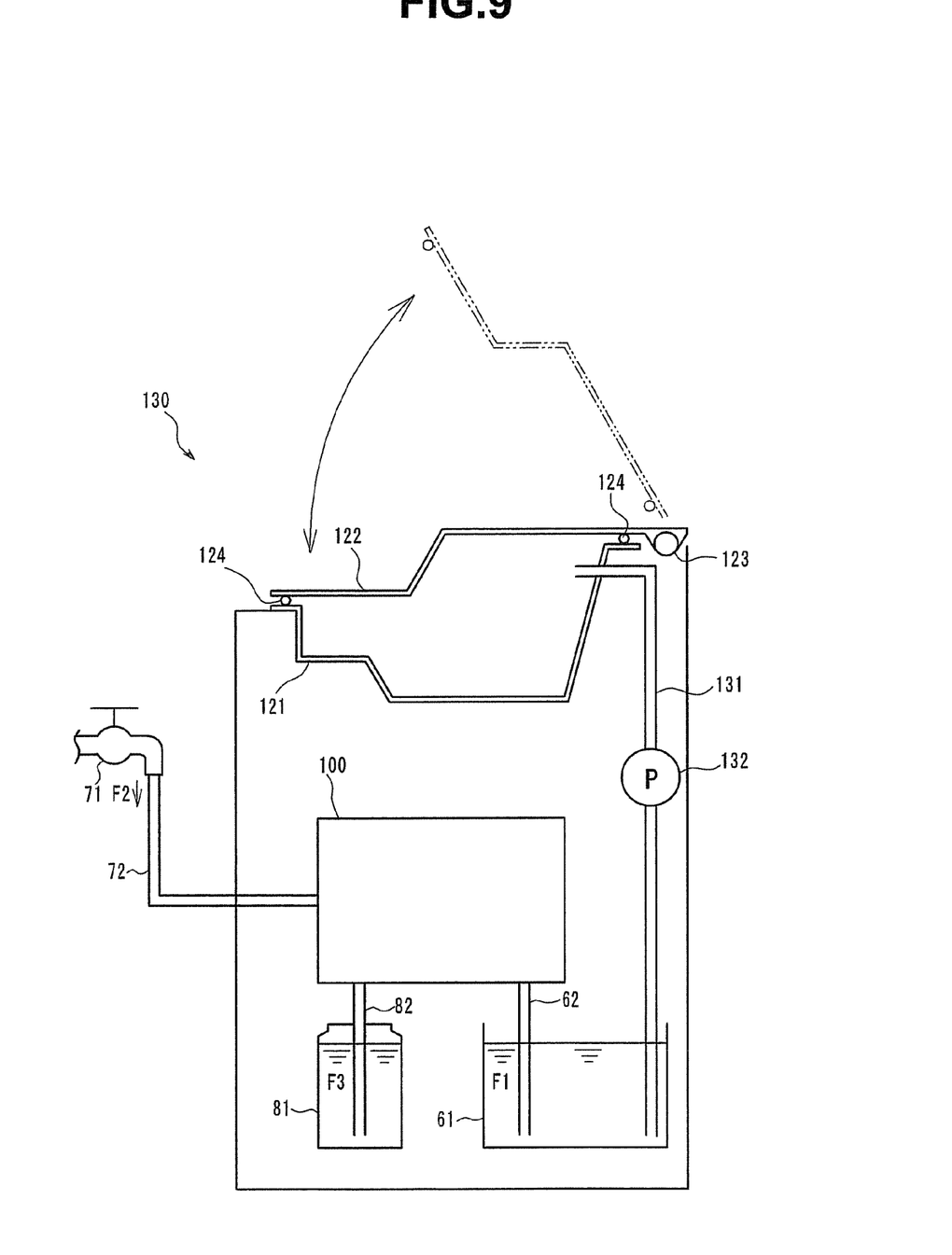
FIG. 9 is a view that describes a configuration of an endoscope processing apparatus according to a fourth embodiment.

A fourth embodiment of the present invention is described hereunder referring to FIG. 9. Only the differences with respect to the second embodiment are described hereunder, and components that are the same as in the second embodiment are denoted by the same reference symbols, and a description of such components is omitted as appropriate.

An endoscope processing apparatus 130 according to the present embodiment includes the chemical testing apparatus 100 and the processing tank 121. The endoscope processing apparatus 130 performs at least one of a cleaning process and a disinfection process using the first liquid F1 that is a chemical stored in the first liquid supply section 61 as a storage tank with respect to an unshown endoscope accommodated in the processing tank 121 which is capable of accommodating the endoscope.

The processing tank 121 is a tub-shaped container that is capable of storing a chemical and that has a shape that can accommodate an endoscope. The processing tank 121 is provided with the lid portion 122 that opens and closes an opening portion thereof. The lid portion 122 is supported by the hinge portion 123, and is rotatable between a closed position at which the lid portion 122 closes the opening portion of the processing tank 121 and an open position at which the lid portion 122 opens the opening portion.

Packing 124 is arranged in the processing tank 121 so as to be interposed between the lid portion 122 and the opening portion of the processing tank 121 in a state in which the lid portion 122 is at the closed position. By means of the above configuration, the opening portion of the processing tank 121 can be hermetically sealed during processing of an endoscope.

The processing tank 121 is connected to the first liquid supply section 61 through a chemical transfer conduit 131. A pump 132 is arranged in the chemical transfer conduit 131. A chemical stored in the first liquid supply section 61 is introduced into the processing tank 121 through the chemical transfer conduit 131 by means of the pump 132.

As described according to the second embodiment, the chemical testing apparatus 100 is arranged so as to conduct an efficacy test with respect to the first liquid F1 that is a chemical that is stored in the first liquid supply section 61. More specifically, after generating a preliminary liquid mixture by mixing the first liquid F1 and the second liquid F2 that is tap water at a predetermined ratio, the preliminary liquid mixture is mixed with a third liquid that is a reagent to thereby generate a liquid mixture. Subsequently, the chemical testing apparatus 100 measures the absorbance of the liquid mixture, and outputs the result of the efficacy test of the chemical.

The result of the efficacy test of the chemical is outputted as an electrical signal to an unshown control section of the endoscope processing apparatus 130. Based on the efficacy test result, the endoscope processing apparatus 130 judges whether or not to execute processing of the endoscope using the chemical that is currently being used. When the endoscope processing apparatus 130 judges that the efficacy of the chemical is insufficient based on the efficacy test result, for example, the endoscope processing apparatus 130 outputs a warning sound or an image or the like to prompt the user to replace the chemical.

As described above, by including the chemical testing apparatus 100, the endoscope processing apparatus 130 according to the present embodiment can automatically judge the efficacy of a chemical to be used to process an endoscope. Further, as described in the second embodiment, because the chemical testing apparatus 100 has a simple configuration, the endoscope processing apparatus 130 of the present embodiment can also be made with a simple configuration, and it is easy to miniaturize the endoscope processing apparatus 130 and decrease the manufacturing cost thereof.

In this connection, according to the present embodiment as shown in FIG. 9 the chemical testing apparatus 100 has a form in which the first liquid supply section 61 is arranged as a storage tank that is provided inside the endoscope processing apparatus 130, and a chemical is extracted from the storage tank. However, a configuration may also be adopted in which the first liquid supply section 61 is the processing tank 121. More specifically, a configuration may be adopted in which an efficacy test is conducted with respect to a chemical that is stored inside the processing tank 121. Further, the endoscope processing apparatus 130 may have a form that also includes the liquid mixing apparatus 1 of the first embodiment.

The present invention is not limited to the above-described embodiments, and can be modified as appropriate within a range that does not depart from the spirit and scope of the invention that can be read from the claims and the entire description. A liquid mixing apparatus, a chemical testing apparatus, and an endoscope processing apparatus including such modifications are also included in the technical scope of the present invention.

What is claimed is:

1. An endoscope processing apparatus comprising;
a liquid mixing apparatus for mixing a plurality of liquids, the liquid mixing apparatus comprising:
a first tank;
a first liquid level sensor provided inside the first tank;
a second liquid level sensor provided inside the first tank, the second liquid level sensor detecting a liquid level higher than a liquid level that the first liquid sensor detects;
a first introduction section that introduces a first liquid into the first tank;
a second introduction section that introduces a second liquid into the first tank;
a first opening portion that is provided above a highest liquid level of the first tank;
a second tank;
a third liquid level sensor provided inside the second tank;
a fourth liquid level sensor provided inside the second tank, the fourth liquid level sensor detecting a liquid level higher than a liquid level that the third liquid sensor detects;
a third introduction section that introduces a third liquid into the second tank;
a second opening portion that is provided above a highest liquid level of the second tank;
a liquid transfer conduit having one end arranged below a lowest liquid level in the first tank and another end connected to the second tank;
an opening/closing valve that is provided in the liquid transfer conduit;
a gas transfer conduit having one end arranged above the highest liquid level in the first tank and another end arranged above the highest liquid level in the second tank;
a pump capable of forward/reverse operation that is provided in the gas transfer conduit and that can transfer a gas in two directions inside the gas transfer conduit; and
an atmospheric release control section that controls opening and closing of the first opening portion and the second opening portion;
a processing tank adapted to hold the endoscope and operably connected to the second tank; and a control section that is operably connected to the first liquid level sensor, the second liquid level sensor, the third liquid level sensor, the fourth liquid level sensor, the first introduction section, the second introduction section, the pump capable of forward/reverse operation and the atmospheric release control section, and controls the first introduction section, the second introduction section, the pump capable of forward/reverse operation and the atmospheric release control section based on a detection result of one or more of the first liquid level sensor, the second liquid level sensor, the third liquid level sensor and the fourth liquid level sensor.

2. The endoscope processing apparatus according to claim 1, in which the atmospheric release control section is a three-way valve comprising a first port that is connected to the first opening portion, a second port that is connected to the second opening portion, and a third port that is open to an atmosphere, wherein:
the atmospheric release control section is switchable between a state in which the first port and the third port communicate and the second port is blocked, and a state in which the second port and the third port communicate and the first port is blocked.

3. The endoscope processing apparatus according to claim 1, wherein:
the first introduction section comprises a check valve that allows a flow of a fluid only in a direction from a first liquid supply section that supplies the first liquid towards an inside of the first tank; and
the third introduction section comprises a check valve that allows a flow of a fluid only in a direction from a third liquid supply section that supplies the third liquid towards an inside of the second tank.

4. The endoscope processing apparatus according to claim 1, further comprising a chemical testing apparatus configured to test a chemical in the second tank of the liquid mixing apparatus.

* * * * *